(12) United States Patent
Nakagawa

(10) Patent No.: US 7,503,654 B2
(45) Date of Patent: Mar. 17, 2009

(54) PUPIL REACTION ASCERTAINING DEVICE AND FATIGUE RECOVERY PROMOTING DEVICE

(75) Inventor: Akio Nakagawa, Kyoto (JP)

(73) Assignee: Woc Co., Ltd, Kyoto-shi, Kyoto (JP)

( * ) Notice: Subject to any disclaimer, the term of this patent is extended or adjusted under 35 U.S.C. 154(b) by 0 days.

(21) Appl. No.: 10/593,881

(22) PCT Filed: Mar. 16, 2005

(86) PCT No.: PCT/JP2005/004684

§ 371 (c)(1),
(2), (4) Date: Apr. 13, 2007

(87) PCT Pub. No.: WO2005/096917

PCT Pub. Date: Oct. 20, 2005

(65) Prior Publication Data

US 2007/0242223 A1    Oct. 18, 2007

(30) Foreign Application Priority Data

Mar. 30, 2004   (JP)   ............................... 2004-100427

(51) Int. Cl.
*A61B 3/10* (2006.01)
(52) U.S. Cl. ........................................ 351/221; 351/204
(58) Field of Classification Search ................. 351/200, 351/204, 221
See application file for complete search history.

(56) References Cited

U.S. PATENT DOCUMENTS 6,669,651 B1 * 12/2003 Fukushima et al. ......... 600/558
2004/0105075 A1 * 6/2004 Kandel et al. ............... 351/221

FOREIGN PATENT DOCUMENTS

JP    2002-238853    8/2002

* cited by examiner

*Primary Examiner*—Scott J Sugarman
*Assistant Examiner*—Dawayne A Pinkney

(57) ABSTRACT

It is an object of the present invention to provide a pupillary reflex checking apparatus that enables a subject to check his own pupillary reflex and that keeps down cost and to provide a fatigue recovery facilitating apparatus that includes the pupillary reflex checking apparatus. The pupillary reflex apparatus of the present invention includes, as essential elements of its structure, a reflecting unit and a stimulus applying unit. Of these, the reflecting unit has a structure which includes an optical reflecting surface disposed in a plane that intersects with a visual axis of a subject such that an image of a pupil of a subject's eye is formed on the optical reflecting surface. Further, the stimulus applying unit applies a stimulus to induce the pupillary reflex in the subject. Specifically, it is possible to use a light source which gives a light stimulus to the subject's eye, such as an LED light source, an electric bulb, a strobe, or the like, as the stimulus applying unit.

9 Claims, 4 Drawing Sheets

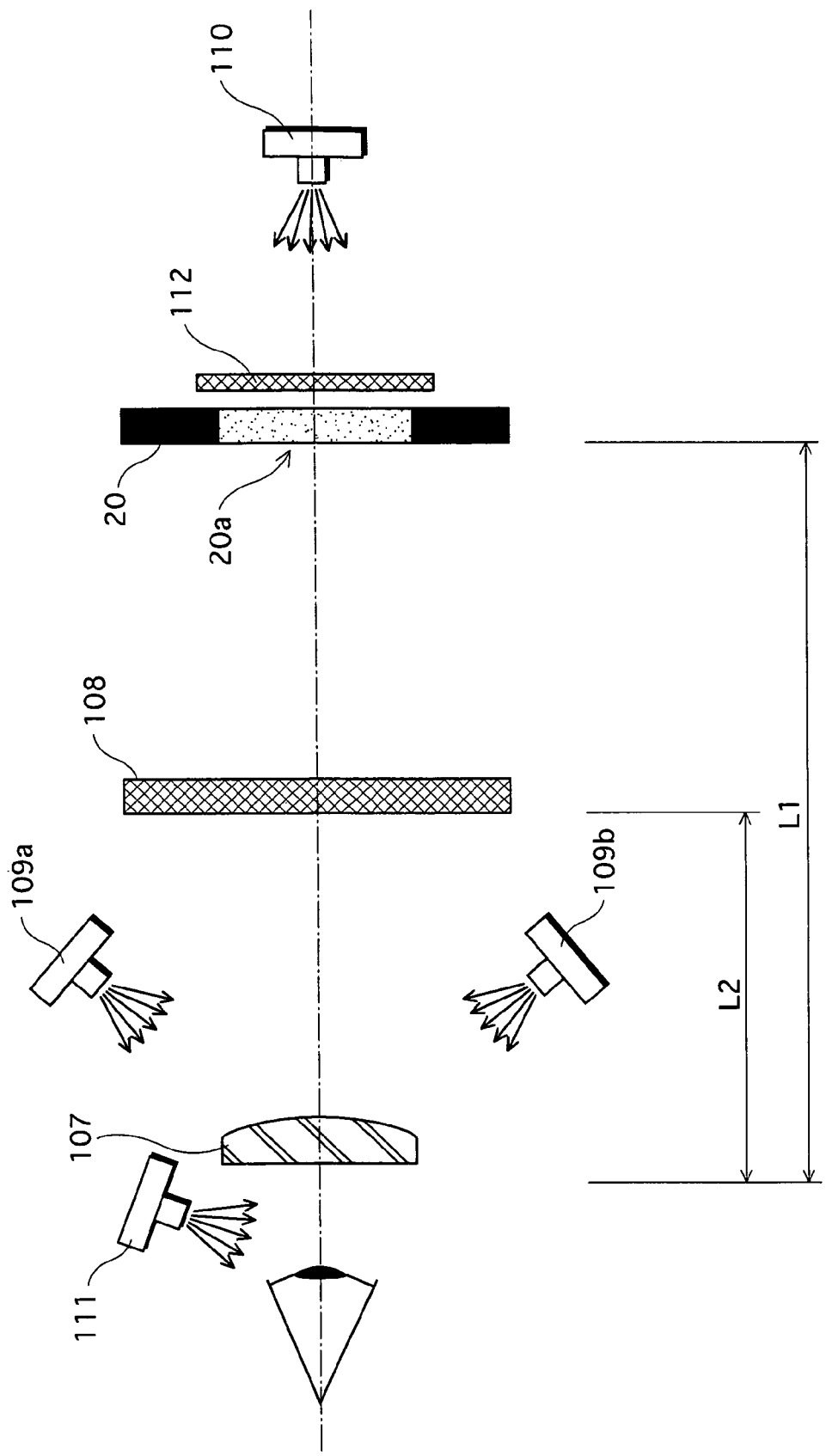

PUPIL REACTION ASCERTAINING DEVICE AND FATIGUE RECOVERY PROMOTING DEVICE

TECHNICAL FIELD

The present invention relates to a pupillary reflex checking apparatus and a fatigue recovery facilitating apparatus which includes the pupillary reflex checking apparatus.

Background Art

In recent years, eye conditions, such as eye strain and "techno-stress" (Chronic Fatigue Syndrome), caused by working with VDTs (Visual Display Terminals) such as those used in PCs (Personal Computers) have become a significant object of public concern. Eyestrain and the like occur because modern working conditions, under which long periods are spent at VDTs or the like, cause the ciliary muscle and other muscles of the eye to be tensed continually, making them difficult to relax.

Conventionally, methods such as telescopic methods, convex lens apparatus methods, eyedrop treatment methods, and the like have been used to facilitate recovery from conditions such as eye strain, but in recent years, apparatus which use "fogging" to relax the ciliary muscle and facilitate recovery from eye strain and the like have been developed. One fatigue recovery facilitating apparatus using such a fogging method has a subject look through infinity optical system ocular lenses at optotype charts (the specimen being an image of a landscape, or the like) provided inside the apparatus for the left and right eyes respectively, thereby using the principal of looking into infinity to ease the strain on the ciliary muscles. By using the apparatus for a certain period, the subject is able to ease the strain in ciliary muscles which have been continually tensed for a lengthy period, and to facilitate his recovery from eyestrain or the like.

However, such an effect is difficult to achieve in practice because, if eyestrain is to be eased using the apparatus, the subject must for a certain period do nothing but stare at the optotype charge inside the apparatus. Thus, it is difficult o have the subject continue using the apparatus in the long term. If, however, the subject is able to see his pupillary state changing between a state of mydriasis and one of miosis through his use of the apparatus, it is conceivable that such long-term use will be achieved. Methods to measure pupil size using for instance an apparatus which measures pupil size using a CMOS (Complementary Metal-Oxide Semiconductor) image sensor, have been developed (See Patent Document 1), and it is theoretically possible that such teclmiques will be applied in fatigue recovery facilitating apparatuses.

Patent Document 1: Japanese laid-open patent application No. 2002-238853

DISCLOSURE OF THE INVENTION

Problems that the Invention Aims to Solve

However, existing techniques, such as the one of the Patent Document 1, are problematic in that it is difficult for the subject to check his own pupillary reflex while using the apparatus, and in that the cost of the apparatus will increase because of its more complex structure. For reasons such as this, it is difficult to apply the technology of Patent Document 1 in apparatuses such as the fatigue recovery facilitating apparatus.

The present invention aims to solve these problems, and has the particular object of providing a pupillary reflex checking apparatus that enables the subject to check his own pupillary reflex and a fatigue recovery facilitating apparatus which includes the pupillary reflex apparatus, while suppressing any increase in cost.

Means to Solve the Problem

In order to solve these problems the pupillary reflex checking apparatus of the present invention includes: a reflecting unit operable to form an image of a pupil of a subject's eye on an optical reflecting surface that is disposed in a plane that intersects with a visual axis of the subject; and a stimulus applying unit operable to apply a stimulus to induce a pupillary reflex in the subject.

Here, it is possible to adopt a structure in which for instance an LED or the like is used to give a light stimulus to the subject's eye. For the purposes of observing the pupillary reflex, it is preferable that pulses of a high quantity of light are used. Further, with regard to the manner in which the optical reflecting surface is disposed in the construction, though the optical surface is described as intersecting with the visual axis of the subject, if a means of refraction such as a mirror is inserted between the subject's eye and the optical reflecting surface, the refracted line of vision will become the basis for positioning the optical reflecting surface.

When pulsed light is used to irradiate a subject's eye in this way, it is preferable to set the emission period to be as long as, or longer than, the period for mydriasis and miosis. When the pupils of a human being have been caused to contract by means of a light stimulus or the like, once the stimulus is removed they require a minimum of 0.6 seconds to 0.7 seconds to dilate to their original state, and consequently, if the emission period of the light pulses is set to be shorter than this, it will not be possible to observe a correct pupillary reflex. If, on the other hand, the emission period of the pulsed light is set to be as long as, or longer than, the period for mydriasis and miosis, the subject will be able to correctly observe his pupillary reflex. Furthermore, it is preferable, when human psychological characteristics pertaining to the perception of brightness are taken into consideration, to set the ratio of emission time to emission period for the pulsed light, this being the percentage of the light and dark states occupied by the light state, to be substantially (60±20% for example).

Further, it is preferable to provide the pupillary reflex checking apparatus with an illumination unit which irradiates the subject's eye with a lower quantity of light than the pulsed light emitted from the stimulus applying unit, as this will enable the subject to check his pupils even when there is insufficient background light for him to do so, such as when no pulsed light stimulus is being applied to the subject's pupils and they are in miosis. Provided that the light from the illumination unit reaches the subject's eye, there are no particular limits as to where it is installed, though it is preferable that it is provided out of the subject's visual axis so as not to be a hindrance when he is checking his pupillary reflex.

In the pupillary reflex apparatus of the present invention, a half-mirror can be used to realize the reflecting unit. When this is the case, the half-mirror is disposed in the subjects's visual axis.

Further, the fatigue recovery facilitating apparatus of the present invention includes a pupillary reflex checking unit that lets a subject check his own pupils, the pupillary checking means having the same structure as the pupillary checking apparatus. Further, it is possible for this apparatus to have a construction in which the reflecting unit is composed of a half mirror. It is further possible, when the stimulus applying unit is a light source capable of irradiating the pupils with pulsed light, to have a construction in which a) an image display unit is provided in the subject's visual axis on the extension of an imaginary line linking his eye and the reflecting unit, and b) an ocular lens is provided in the subject's visual axis in proximity to his eye. Here, it is preferable to use an infinity optical system or the like as the ocular lens.

In the apparatus, it is preferable to set the optical distance between the ocular lens and the reflecting unit to be substantially 50% (50±20%, for example) of the optical distance between the ocular lens and the image display unit.

Further, in the fatigue recovery facilitating apparatus of the present invention, it is preferable, in view of the fact that fogging is to be used, to provide at least an image display unit and ocular lens for each of the left and right eyes of the subject.

EFFECTS OF THE INVENTION

Since the pupillary reflex checking apparatus pertaining to the present invention and having the above structure includes the optical reflecting surface of the reflecting unit disposed in a direction intersecting with (and substantially perpendicular to) the subject's visual axis, and includes a stimulation applying unit for inducing the pupillary reflex in the subject, the subject is able to observe in real time the image of his pupils as they receive a stimulus from the stimulation applying unit. With this apparatus, even without using for instance a CMOS sensor in the manner of Patent Document 1, the subject can easily check his pupillary reflex, and it is therefore possible for a cost advantage to be obtained and for the subject to check his own pupillary reflex in real time.

This type of pupillary reflex checking apparatus can be incorporated into various apparatuses, but the effect is especially desirable when it is used in the fatigue recovery facilitating apparatus. Due to the incorporation of the pupillary reflex checking apparatus into the fatigue recovery facilitation apparatus, when the subject looks into the apparatus to alleviate the strain in his ciliary muscles and encourage recovery from fatigue, he is able, after a predetermined period, to visually check his pupillary reflex by temporarily switching from the optical system to the system for checking the pupillary reflex. Further, the subject is able, after checking the state of his pupillary reflex, to repeat the process for alleviating strain in his ciliary muscles. Since the subject can check his own pupillary reflex as his eyes undergo fatigue recovery, he can see the effect that the apparatus is having, and can be encouraged to use it regularly.

Note that the pupillary reflex checking apparatus of the present invention can be applied in apparatuses other than the fatigue recovery facilitating apparatus, including for instance apparatuses that test brain functions using the pupillary reflex, apparatuses for performing tests on the eyes, and the like.

BRIEF DESCRIPTION OF THE DRAWINGS

FIG. 3 is a schematic showing a structure which is for checking the pupillary reflex and is included in the fatigue recovery facilitating apparatus 1.

Figure 1:
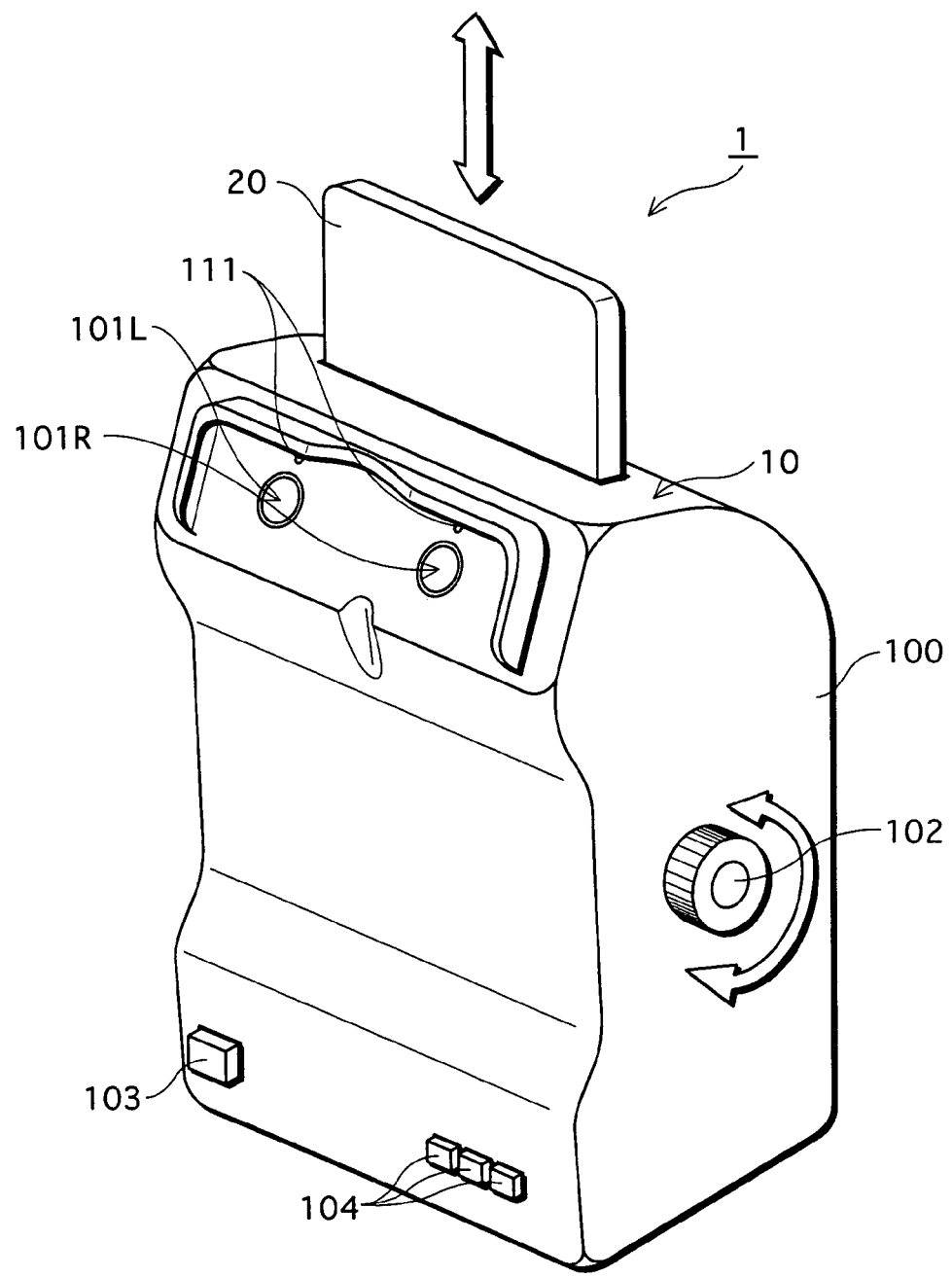
FIG. 1 is a perspective view of an exterior of a fatigue recovery facilitating apparatus 1 of the embodiment of the present invention.

DESCRIPTION OF CHARACTERS 1 fatigue recovery facilitating apparatus
10 body
20 optotype chart
107 ocular lens
108 half-mirror
109a, 109b, 110, 111 LED light source
112 light scattering board
500 pupil
501 iris
502 ciliary muscle
503 zonnules of Zinn
504 crystalline lens
505 vitreous body

BEST MODE FOR CARRYING OUT THE INVENTION

The preferred embodiment of the present invention is described with reference to FIGS. 1 to 4. Hereafter, the characteristics and effects arising from the structure of the present invention are described using the fatigue recovery facilitating apparatus 1 as an example, but it is noted in advance that the present invention is not limited to what is described.

(Structure of Fatigue Recovery Facilitating Apparatus 1)

Firstly the overall structure of the fatigue recovery facilitating apparatus 1 is described using FIG. 1. FIG. 1 is a perspective view of the exterior of the fatigue recovery facilitating apparatus 1 of the embodiment of the present invention.

As shown in FIG. 1, the fatigue recovery facilitating apparatus 1 of the present embodiment is composed of a body 10 and a optotype chart 20 inserted for use therein. Of these, the body 10 includes a housing 100 which is substantially a rectangular parallelepiped (a parallelepiped with added irregularities), and viewfinders 101L and 101R which are provided in an upper region of a front of the housing 100. Further, a power switch 103 and exchange switches 104 for changing the operating period are provided in a lower region of the front of the body 100, and a dial 102 to enable the subject, or someone else, to move the optotype chart 20 up and down is provided on a side of the body. Note that the exchange switches 104 also function as operation starting switches for starting the operation of the apparatus 1. When, for example, the user wishes to operate the apparatus 1 with the operating period set to five minutes, he can do this by switching on the power switch 103 and subsequently pushing the exchange switch 104 indicating a five minute time setting.

Further, a short distance above the viewfinders 101L and 101R of the fatigue recovery facilitating apparatus 1, LED light sources 111 are provided to illuminate the eyes of the subject.

Figure 2:
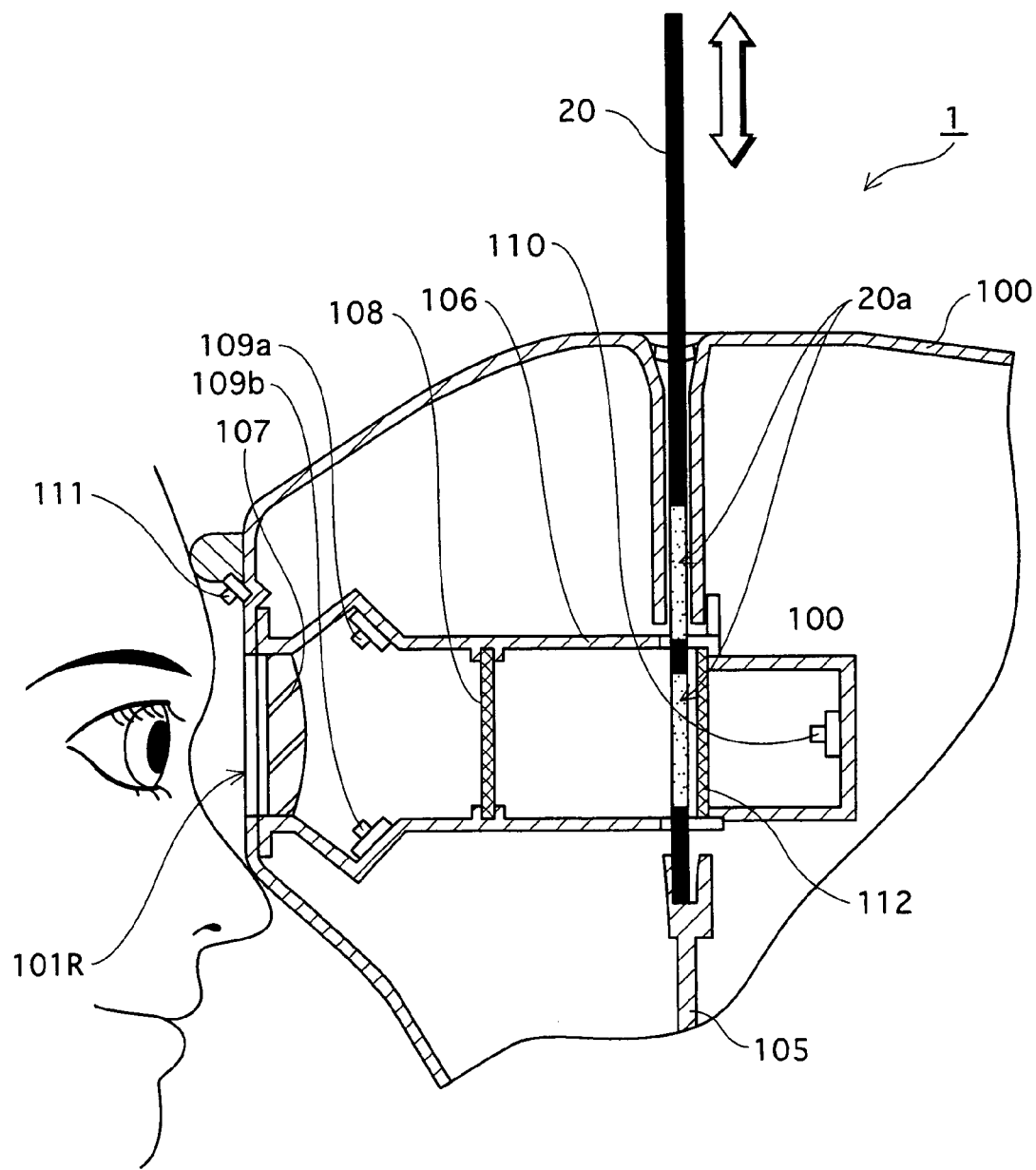
FIG. 2 is a cross-section showing main parts of the fatigue recovery facilitating apparatus 1.

Next, structures of the main parts of the fatigue recovery facilitating apparatus 1 are described using FIG. 2. FIG. 2 shows part of the fatigue recovery facilitating apparatus 1 shown in FIG. 1 cross-section. Note that though FIG. 2 shows only the portion corresponding to the right eye of the subject, in the fatigue recovery facilitating apparatus 1 of the present embodiment, an optical system for the left eye which has the same structure as the system for the right eye shown in FIG. 2 is provided in parallel with the optical system for the right eye (in such a way that the viewing direction for each eye remains parallel to the other).

As shown in FIG. 2, the viewfinder 101R is provided immediately in front of the subject's eye in the subject's visual axis and inside the housing 100 of the body 10 as described above, and an internal body 106 encompassing a region in which the visual axis falls is provided thereafter. The internal body 106 includes an ocular lens 107 positioned in proximity to the view finder 101R, and a half-mirror 108 provided so as to be a short distance away from the ocular lens 107. Further, an LED light source 110 is provided in a position that opposes the view finder 101R in the body 106. Here, an infinity optical system lens is used as the ocular lens 107. Further, since the image film 20a of the optotype chart 20 is located at the focal point of the ocular lens 107, parallel beams of light enter the eye of the subject.

Further, as described above, the illumination-use LED light source 111 is provided a short distance above the viewfinder 101R. This LED light source 111 is provided so that the subject's eyes can be illuminated when he uses the fatigue recovery facilitating apparatus 1 in a environment which is otherwise too dark for him to see them. Note that the illumination-use LED light source 111 is located off the visual axis of the subject, and that its brightness is set to be considerably lower the LED light sources 109a and 109b that are described later.

The optotype chart 20 is inserted between the half-mirror 108 and the LED light source 110 and in such a way that it can be moved up and down in a direction that intersects with the direction of the subject's visual axis (the horizontal in FIG. 2). Further, a plurality of pairs of image films 20a, each pair composing an image for each of the left and right eyes, are formed in a region of the optotype chart 20. Further, the optotype chart 20 is held by a recipient lever 105 which is connected to, and moved up and down by, the dial 102 provided on the side of the housing 100, and the optotype chart 20 moves up and down as the subject turns the dial. The optotype chart 20 is constructed in this way so that the subject can make a selection from the image film 20a.

The LED light source 110 is for lighting the image film 20a from, what is to the subject, the back side thereof, and flashes on and off repeatedly with a predetermined period. Further, the light scattering board 112 is provided between the LED light source 110 and the image film 20a. This is provided to scatter the light emitted by the LED light source 110.

Further, the LED light sources 109a and 109b are provided in a position that will not obstruct the visual axis of the subject when he is observing one of the image films 20a of the optotype chart 20. The two LED light sources 109a and 109b emit, when the LED light source 110 is temporarily OFF, pulsed light with a predetermined period towards the eyes of the subject, and these pulses are brighter than the light emitted from the LED light source 111 which is provided for the purposes of illumination. In other words, in the fatigue recovery facilitating apparatus 1, when the LED light source 110 is temporarily OFF, the subject's eyes are irradiated by light of a low intensity from the LED light source 111 and by pulses of high intensity light with a predetermined period from the LED light sources 109a and 109b.

It is preferable that the flashing cycle period of the LED light sources 109a and 109b is same length as the period of mydriasis and miosis in the subject, though a period longer than the period of mydriasis and miosis may be also be used. In the present embodiment the flashing frequency for the LED source 109a and 109b can be set to be approximately 20 pulses/minute.

Further it is preferable that the pulse width of the pulsed light from the LED light sources 109a and 109b is set to be approximately 60% of the width of one flashing cycle period (60±20%, for instance). In other words, the ratio of the length time that light is emitted from the light sources 109a and 109b to the length time that light is not emitted is set to be 3:2. This is because setting ratio of the length of the "light" state to the length of the "dark" state to be 3:2 causes the mind to perceive that the light and dark states are equally distributed.

The fatigue recovery facilitating apparatus 1 of the present embodiment has a structure such as the one described above. However, provided that the structure includes the characteristics noted in the "means to solve the problem" section, the present invention is not limited to the above structure, and suitable modifications are possible.

(Functions of Fatigue Recovery Facilitating Apparatus 1)

Of the functions of the fatigue recovery facilitating apparatus 1, those which are characteristic of the present embodiment are described using FIG. 3 and FIGS. 4A-4D. FIG. 3 is a schematic showing the fatigue recovery facilitating apparatus functions which are characteristic of the present embodiment. FIGS. 4A-4D are schematics showing the changes state that occur in a subject's pupil and eyeball when the fatigue recovery facilitating apparatus 1 is used.

As shown in FIG. 3, from the subject's end, the ocular lens 107, the half-mirror 108, the image film 20a of the optotype chart 20, and the LED light source 110 are disposed in the subject's visual axis in the stated order. Further, as shown in FIG. 2 the LED light sources 109a and 109b are disposed in proximity to the half mirror 108 in upper and lower positions respectively for the purpose of stimulating the eye. Moreover, the light scattering board 112 is provided between the LED light source 110 and the image film 20a.

Regarding the locations of the structural elements in relation to the subject's eyeball, the ocular lens 107 is located in proximity to the eyeball as described above, the image film 20a of the optotype chart 20 is disposed a distance L1 from the ocular lens 107, and the half-mirror 108 is disposed a distance L2 from the ocular lens. Here, the relationship between the distance L1 and the distance L2 is set so that the distance L2 is substantially 50% of the distance L1 (50±20% the distance L1, for instance). The position of the half-mirror 108 is set in this way with distance L2 being substantially 50% of the distance L1 so that when the subject observes his eyeball the image passes through the eyepiece 107 lens twice.

With the above structure, a virtual image of the subject's eyeball is formed on the image film 20a of the optotype chart 20, and after the LED light source 110 has been switched off, the subject is able, by means of the LED light sources 109a and 109b which start to flash, to check his pupillary state which is reflected in the half mirror 108. Hence, by means of the present apparatus 1, the subject can look at the image film 20a in order to facilitate his recovery from fatigue, and at the same time and using the same apparatus, check his pupillary state. In short, he can check mydriasis or miosis.

Note that the illumination-use LED light source 111 is disposed in a position between the subject's eye and the ocular lens 107 and off visual axis.

The relationship between the operating state of the fatigue recovery facilitating apparatus 1 and the state of the subject's eye is described below.

At the beginning of operations of the fatigue recovery facilitating apparatus 1, the subject observes the image film 20a of FIG. 3, which the LED light source 110 is repeatedly illuminating with flashes of a predetermined period. When the subject is observing the image film 20a in this way, light which has passed from the LED light source 110 and through the image film 20a enters the subject's eyes as parallel rays. Observing the image film 20a, whose images are being repeatedly projected by the LED light source 110 with flashes of a predetermined period in this way, effectively enables the subject to look at an image at infinity and ease the tension of his ciliary muscles. Subsequently, after the flashing operation of the light source 110 has been repeated for a predetermined length of time, the LED light source 110 is temporarily switched off. In its place, the flashing operation of the LED light sources 109a and 109b then begins.

Note that, though in the present embodiment a structure to have the light from the LED light source 110 enter the subject's eye as parallel rays was described, the light does not necessarily have to enter as parallel rays. It is also possible to use a structure to have, for example, the light enter as diffused (scattered) light, or a structure to have the light enter as condensed light.

Figure 4A:
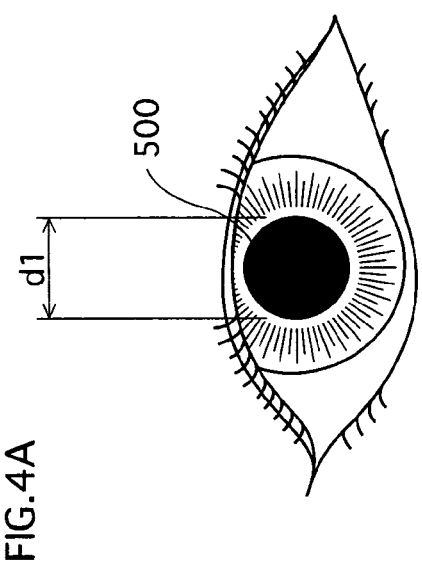
FIGS. 4A-4D are conceptual drawings showing the pupillary reflex shown by a subject using the fatigue recovery facilitating apparatus 1.
Figure 4B:
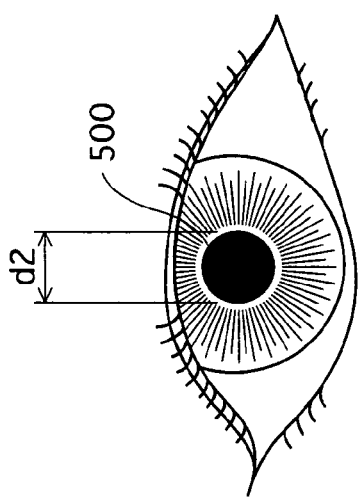
Figure 4C:
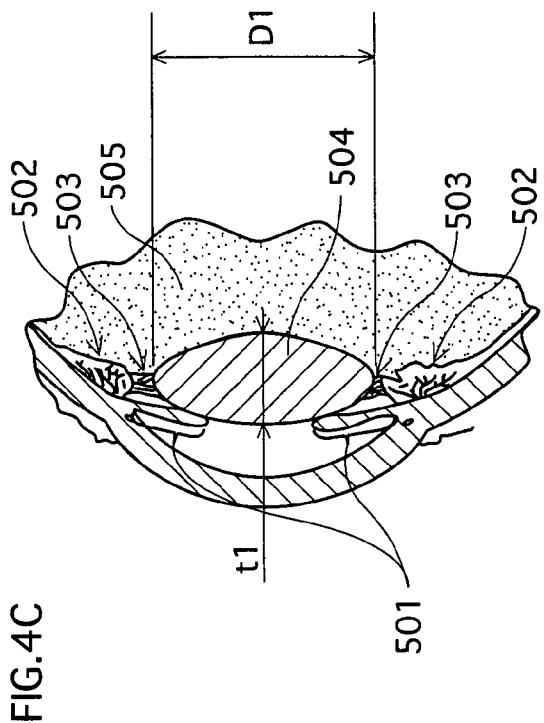

When the LED light sources 109a and 109b are OFF, only light from the LED light source 111 enters the subject's eye, and under such conditions, the subject's pupil 500 moves into a state of mydriasis taking a diameter d1, as shown in FIG. 4A. When the pupil 500 is in a state of mydriasis, the ciliary muscle 502 surrounding the vitreous body 505 moves into a relaxed state and the iris into a stretched state, which results in an enlarging of the pupil, as shown in FIG. 4C.

Figure 4D:
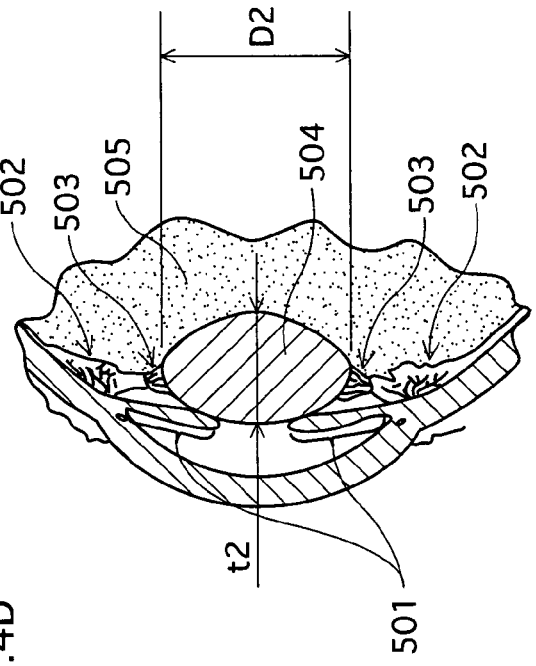

Next, when the LED light sources 109a and 109b are ON, a stimulus of intense light is applied to the subject's eye. The subject's pupil 500 receiving the stimulus of intense light moves into a state of miosis, as shown in FIGS. 4B and 4D, taking a diameter of d2, which is smaller than d1. At this point, the ciliary muscle is in a tensed state.

In the fatigue recovery facilitating apparatus 1 of the present embodiment, the LED light sources 109a and 109b are flashed on and off at a predetermined frequency (20 pulse/min for instance), and as the subject observes the image film 20a to encourage his eyes to recover from fatigue, his pupillary state is caused to cycle between a state of mydriasis and one of miosis. Visually checking this cycle enables the subject to perceive the effects of the fatigue recovery facilitating apparatus 1. With subject being able to check mydriasis and miosis in this way, he can be positive about using the apparatus 1 in the long term. Here, even when the LED light sources 109a and 109b are off, the subject can check for mydriasis because the LED light source 111 is constantly switched on for the purposes illumination. It is to be noted however that, as described above, the intensity of the light emitted from the LED light source 111 is set to be lower than that of the light emitted from the LED light sources 109a and 109b for stimulating the eyes of the subject.

Note that, if room lighting is sufficiently bright, the LED light source 111 need not be included. Further, room brightness may be sensed, and the LED light source be switched on or off accordingly.

(Supplementary Remarks)

As described above, the fatigue recovery facilitating apparatus 1 is one example of the present invention, one which has been used for the purposes of explaining the characteristics relating to the structure of the present invention and the effects achieved as a result of these characteristics. However, the present invention is not limited by this example. For example, in the fatigue recovery facilitating apparatus 1, the LED light sources 109a and 109b emitting pulsed light are provided as a means to apply a stimulus to the eyes in order to change the state of the pupils from a state of mydriasis to one of miosis. However, the light used to stimulate the eyes is not limited to being from an LED light source, but may be from another light source, such as an electric light bulb, a strobe, or the like. Further, a means for applying a stimulus other than light (such as sound, for instance) may be provided.

Further, though the fatigue recovery facilitating apparatus 1 was described as having a structure in which the optotype chart 20 was positioned in the subject's visual axis, it is possible to provide a different optotype chart, in an upper section of the apparatus for instance, and to have the subject observe the image of the upper optotype chart by disposing a half-mirror between the subject and the upper optotype chart at a 45 degree angle. The reason for further disposing a optotype chart in the upper section in this way is that, as opposed to when the subject observes the front image film and the light enters his eye in parallel beams, when the subject observes the upper optotype chart, he perceives that the image is, for instance, 1 m in front of his eye (in an empty field). This means that it is possible, by having the subject observe the front chart and the upper chart alternately, to further encourage the subject's ciliary muscles to relax.

Further, though in the embodiment the half-mirror 108 is described as being of a fixed type, it does not have to be fixed. For example, the half-mirror 108 may be of a movable type so that it can be removed from the subject's visual axis, and the apparatus may be composed in such a way that the subject can remove the half-mirror from his visual axis as and when he wishes.

Further, a means other than a half-mirror may be used to enable the subject to check his pupillary reflex. For example, a structure may be used in which the subject's pupils are observed using an image sensor or the like and a monitor which shows this pupil-related information is provided in proximity to the optotype chart 20.

Further, with regard to the above embodiment, though the characteristics of the present invention are described using the fatigue recovery facilitating apparatus 1 which is for facilitating recovery from eye-strain and the like, if the half-mirror 108 and LED light sources 109a and 109b are added to an eyesight testing apparatus or the like, the advantage of the subject being able to check the state of his pupils in the way described above can be obtained. Moreover, the present invention can also be applied in an apparatus for preventing, and facilitating recovery from, progressive myopia.

Moreover, though in the embodiment the LED light sources 109a and 109b for giving a light stimulus to the subject's eyes and the LED light source 111 for illumination are separately provided, a structure in which one of the light sources, such as LED light source 111 for instance, is made to fulfill both functions can be used.

Note that, in FIG. 2, the LED light sources 109a and 109b, the LED light source 111 and the half-mirror 108 are an optical system constructed to enables the subject to observe his own pupils, and that the optotype chart 20, LED light source 110 and the like compose a separate optical system.

INDUSTRIAL APPLICABILITY

The present invention is effective for realizing an apparatus for facilitating recovery from fatigue such as techno-stress and eyestrain caused by working with the VDTs of personal computers and the like, an apparatus for preventing and facilitating recovery from progressive myopia, or other such apparatuses.

The invention claimed is:

1. A fatigue recovery facilitating apparatus for facilitating recovery from fatigue of a subject by repetition of mydriasis and miosis, the fatigue recovery facilitating apparatus including
    a pupillary reflex checking unit for a subject to check his or her own pupillary reflex, wherein
    the pupillary reflex checking unit includes:
    a reflecting subunit operable to form an image of a pupil of a subject's eye on a half-mirror optical reflecting surface with a main mirror surface that is disposed in a plane that is substantially orthogonal to a visual axis of the subject;

an image display subunit, in the visual axis of the subject, is provided on an extension of an imaginary line that connects an eyeball of the subject and the reflecting subunit;

an ocular lens is disposed in proximity to the eyeball of the subject; and a stimulus applying subunit configured to apply a light stimulus of pulsed light to induce a pupillary reflex in the subject, wherein the image display subunit includes a film and a light source that irradiates the subject's eye with pulsed light through the film.

2. The fatigue recovery facilitating apparatus of claim 1, wherein a period of the pulsed light is set to be at least as long as a period required for mydriasis and miosis.

3. The fatigue recovery facilitating apparatus of claim 1, wherein the pupillary reflex checking unit further includes an illumination subunit operable to irradiate the subject's eye with light that is less intense than the pulsed light irradiated by the stimulus applying subunit.

4. The fatigue recovery facilitating apparatus of claim 1, wherein an optical distance between the ocular lens and the reflecting subunit is substantially 50% of an optical distance between the ocular lens and the image display subunit.

5. The fatigue recovery facilitating apparatus of claim 1, wherein the image display subunit and the lens are one of a plurality of image display subunits and a plurality of lenses, the image display subunits and the lenses being provided with respect to a left eye and a right eye of the subject.

6. A fatigue recovery facilitating apparatus for facilitating recovery from eye strain of a user by a controlled repetition of mydriasis and miosis, comprising:

a compact housing body with left and right view finders and user switch controls on an exterior of the body;

an image display subunit including a light source configured to provide a display image on a visual axis through one of the view finders to the user;

a user control member on the exterior of the housing body to move the display image of the image display subunit;

a reflecting subunit configured to enable a user visible image of a pupil of the user's eye on the visual axis to be seen by the user when the display subunit light source is not activated to provide the display image; and a stimulus applying subunit configured to apply a light stimulus to induce a pupillary reflex in the user wherein the user can activate user switch controls to provide the display image for focusing the user's eyes on the display image and for activating the stimulus applying subunit to induce mydriasis and miosis while enabling the user to observe periodically the effect of the stimulus directly on the image of the user's pupil on the same visual axis.

7. A fatigue recovery facilitating apparatus for facilitating recovery from fatigue of a subject by repetition of mydriasis and miosis, the fatigue recovery facilitating apparatus including a pupillary reflex checking unit for a subject to check his or her own pupillary reflex, wherein the pupillary reflex checking unit includes:

a reflecting subunit operable to form an image of a pupil of a subject's eye on a half-mirror optical reflecting surface with a main mirror surface that is disposed in a plane that is substantially orthogonal to a visual axis of the subject;

an image display subunit, in the visual axis of the subject, is provided on an extension of an imaginary line that connects an eyeball of the subject and the reflecting subunit;

an ocular lens is disposed in proximity to the eyeball of the subject; and a stimulus applying subunit configured to apply a light stimulus of pulsed light to induce a pupillary reflex in the subject, wherein the image display subunit and the ocular lens are one of a plurality of image display subunits and a plurality of lenses, the image display subunits and the lenses being provided with respect to a left eye and a right eye of the subject.

8. The fatigue recovery facilitating apparatus of claim 7, wherein a period of the pulsed light is set to be at least as long as a period required for mydriasis and miosis.

9. The fatigue recovery facilitating apparatus of claim 7, further comprising:

an illumination unit operable to irradiate the subject's eye with light that is less intense than the pulsed light irradiated by the stimulus applying subunit.

* * * * *